US009402571B2

(12) United States Patent
Zhang

(10) Patent No.: US 9,402,571 B2
(45) Date of Patent: Aug. 2, 2016

(54) BIOLOGICAL TISSUE FUNCTION ANALYSIS

(71) Applicant: Siemens Medical Solutions USA, Inc., Malvern, PA (US)

(72) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 14/190,294

(22) Filed: Feb. 26, 2014

(65) Prior Publication Data

US 2014/0180037 A1  Jun. 26, 2014

Related U.S. Application Data

(63) Continuation-in-part of application No. 13/235,612, filed on Sep. 19, 2011.

(60) Provisional application No. 61/430,244, filed on Jan. 6, 2011, provisional application No. 61/804,242, filed on Mar. 22, 2013.

(51) Int. Cl.
*A61B 5/00* (2006.01)
*A61B 5/1455* (2006.01)
*A61B 5/024* (2006.01)
*A61B 5/021* (2006.01)
*A61B 5/046* (2006.01)
*A61B 5/0464* (2006.01)

(52) U.S. Cl.
CPC ......... *A61B 5/14551* (2013.01); *A61B 5/02416* (2013.01); *A61B 5/7264* (2013.01); *A61B 5/7282* (2013.01); *A61B 5/021* (2013.01); *A61B 5/046* (2013.01); *A61B 5/0464* (2013.01); *A61B 5/7203* (2013.01); *A61B 5/7207* (2013.01); *A61B 5/746* (2013.01)

(58) Field of Classification Search
CPC .... A61B 5/04; A61B 5/04012; A61B 5/0205; A61B 5/7285; A61B 5/7264
See application file for complete search history.

(56) References Cited

U.S. PATENT DOCUMENTS

| | | | |
|---|---|---|---|
| 4,860,759 A | 8/1989 | Kahn et al. | |
| 4,960,126 A * | 10/1990 | Conlon | A61B 5/0456 600/336 |
| 5,113,861 A | 5/1992 | Rother | |
| 5,251,632 A * | 10/1993 | Delpy | A61B 5/14553 128/204.23 |
| 5,615,684 A | 4/1997 | Hagel et al. | |
| 6,117,075 A | 9/2000 | Barnea | |
| 6,485,429 B2 | 11/2002 | Forstner | |
| 6,490,480 B1 | 12/2002 | Lerner | |
| 6,511,436 B1 | 1/2003 | Asmar | |

(Continued)

OTHER PUBLICATIONS

Lly Lee, et al., "Pulse oximetry: a survey of knowledge among staff of an emergency department", Hong Kong Journal of Emergency Medicine, vol. 13, No. 4, Oct. 2006, pp. 197-204.

(Continued)

*Primary Examiner* — Manuel Rivera Vargas

(57) ABSTRACT

Disclosed herein is a framework for facilitating biological tissue function analysis. In accordance with one aspect, saturation of hemoglobin with oxygen (SPO2) signal data is synchronized with respiration signal data. One or more waveform parameters may be generated based on the synchronized SPO2 signal data and the respiration signal data. One or more respiration-SPO2 parameters may then be determined based on the one or more waveform parameters and used to characterize the biological tissue function.

19 Claims, 8 Drawing Sheets

(56) References Cited

U.S. PATENT DOCUMENTS

| | | |
|---|---|---|
| 6,616,613 B1 | 9/2003 | Goodman |
| 6,668,182 B2 * | 12/2003 | Hubelbank ........ A61B 5/14551 600/323 |
| 6,709,402 B2 | 3/2004 | Dekker |
| 6,929,610 B2 | 8/2005 | Forstner |
| 6,961,600 B2 | 11/2005 | Kohl et al. |
| 6,987,994 B1 | 1/2006 | Mortz |
| 7,008,380 B1 | 3/2006 | Rees et al. |
| 7,184,809 B1 | 2/2007 | Sterling et al. |
| 7,330,750 B2 | 2/2008 | Erkkla et al. |
| 7,367,949 B2 | 5/2008 | Korhonen et al. |
| 7,794,406 B2 | 9/2010 | Reisfeld et al. |
| 7,806,832 B2 | 10/2010 | Gallagher et al. |
| 7,819,812 B2 | 10/2010 | John et al. |
| 8,200,321 B2 | 6/2012 | McCombie et al. |
| 8,230,858 B2 | 7/2012 | Karlsson |
| 2004/0171948 A1 | 9/2004 | Terry |
| 2004/0267324 A1 | 12/2004 | Geheb et al. |
| 2005/0027207 A1 | 2/2005 | Westbrook et al. |
| 2006/0149144 A1 | 7/2006 | Lynn et al. |
| 2007/0118028 A1 * | 5/2007 | Kitajima et al. .............. 600/310 |
| 2007/0191697 A1 | 8/2007 | Lynn et al. |
| 2007/0239043 A1 | 10/2007 | Patel et al. |
| 2007/0255146 A1 | 11/2007 | Andrews et al. |
| 2008/0051667 A1 | 2/2008 | Goldreich et al. |
| 2008/0055074 A1 | 3/2008 | Gao et al. |
| 2008/0066753 A1 | 3/2008 | Martin et al. |
| 2008/0208009 A1 | 8/2008 | Shklarski |
| 2008/0269832 A1 | 10/2008 | Wong et al. |
| 2009/0131774 A1 | 5/2009 | Sweitzer et al. |
| 2009/0209839 A1 * | 8/2009 | Ochs et al. .................... 600/364 |
| 2009/0240126 A1 * | 9/2009 | Baker et al. .................... 600/324 |
| 2009/0253968 A1 | 10/2009 | Cho et al. |
| 2009/0312648 A1 * | 12/2009 | Zhang ................... A61B 6/541 600/483 |
| 2009/0318787 A1 | 12/2009 | Aoyagi et al. |
| 2010/0087747 A1 | 4/2010 | Lo et al. |
| 2010/0113904 A1 | 5/2010 | Batchelder et al. |
| 2010/0234705 A1 | 9/2010 | Lynn |
| 2011/0040713 A1 * | 2/2011 | Colman et al. .................. 706/16 |
| 2012/0053432 A1 | 3/2012 | Huiku et al. |
| 2012/0150003 A1 | 6/2012 | Zhang |
| 2012/0179382 A1 | 7/2012 | Zhang |
| 2013/0138002 A1 * | 5/2013 | Weng et al. .................... 600/508 |

OTHER PUBLICATIONS

David a Benaron, et al., "Continuous, Noninvasive, and Localized Microvascular Tissue Oximetry Using Visible Light Spectroscopy", Anethesiology, 2004: vol. 100, pp. 1469-1475.

Frederic Series, et al., "Prospective Evaluation of Nocturnal Oximetry for Detection of Sleep-Related Breathing Disturbances in Patients with Chronic Heart Failure", CHEST, Official Publication of the American College of Chest Physicians, vol. 127, No. 5, May 2005, p. 1507-1514.

* cited by examiner

BIOLOGICAL TISSUE FUNCTION ANALYSIS

CROSS-REFERENCE TO RELATED APPLICATIONS

This application claims the benefit of U.S. provisional application No. 61/804,242 filed Mar. 14, 2013, the entire contents of which are incorporated herein by reference.

This application is also a continuation-in-part of co-pending U.S. patent application Ser. No. 13/235,612 filed Sep. 19, 2011 entitled "System for Ventricular Arrhythmia Detection and Characterization," which claims the benefit of U.S. provisional application No. 61/430,244 filed Jan. 6, 2011, all of which are hereby fully incorporated herein by reference.

TECHNICAL FIELD

The present disclosure generally relates to systems and methods for analyzing biological tissue functions.

BACKGROUND

Cardiac arrhythmia is a condition in which the electrical activity of the heart is irregular or is faster or slower than normal. Cardiac arrhythmia may be classified by rate and/or mechanism. For instance, atrial fibrillation (AF) is the most common type of serious arrhythmia that involves a very fast and irregular contraction of the atria. Ventricular fibrillation (VF) is a condition in which there is uncoordinated contraction of the cardiac muscle of the ventricles in the heart. Multifocal atrial tachycardia (MAT) is a type of arrhythmia with an irregular atrial rate greater than 100 bpm. Myocardial ischemia (MI) is a type of arrhythmia that occurs when blood flow to the heart muscle is decreased by a partial or complete blockage of the heart's arteries. Myocardial infarction (commonly known as a heart attack) occurs when blood stops flowing properly to part of the heart and the heart muscle is injured due to not receiving enough oxygen.

Early recognition and characterization of arrhythmia is desirable to prevent progress to a life-threatening arrhythmia, such as atrial fibrillation or ventricular fibrillation. Known methods for cardiac arrhythmia detection and diagnosis focus on electrophysiological data and waveform morphologies, such as a QRS complex, ST segment, T wave, U wave, etc. Typically, a 12-lead electrocardiogram (ECG) and multi-channel intracardiac echocardiography (ICE acquired via invasive cardiac catheters) are used for evaluating cardiac rhythm and events. However, these methods are limited, mainly because an early change of cardiac circulation function is shown first in blood contraction and hemodynamic characteristics, and only subsequently in electrophysiological signals.

Accurate clinical assessment of circulatory status is particularly desirable in critically ill patients in an intensive care unit (ICU) and patients undergoing cardiac, thoracic, or vascular interventions. As patient hemodynamic status may change rapidly, it is necessary to continuously monitor cardiac output so as to obtain information that enables rapid adjustment of therapy. Usually, non-invasive blood pressure (NIBP) monitoring and/or least invasive blood pressure monitoring are used to observe hemodynamic changes in cardiac tissue and function.

Conventional methods for cardiac circulation arrhythmia (e.g., atrial fibrillation or AF, myocardial infarction, etc.) detection and diagnosis based on electrophysiological signal (e.g., ECG, ICEG, etc.) morphologies require extensive clinical knowledge and experience for accurate interpretation. Inaccurate, subjective and non-quantitative evaluation and diagnosis may delay detection of a cardiac condition. Known methods based on hemodynamic blood pressure (e.g., NIBP signals) wave morphology changes also fail to efficiently differentiate various cardiac malfunction arrhythmia types and categorize severity of the arrhythmia pathologies. In addition, known cardiac arrhythmia analysis typically lack efficiency and reliability, and are sensitive to noise. Ventricular activity signals may be obscured by noise and artifacts, especially for small patient signals (uV to mV range).

Accordingly, there exists a need to provide an improved framework to address these deficiencies and related problems.

SUMMARY

The present disclosure relates to a framework for facilitating biological tissue function analysis. In accordance with one aspect, saturation of hemoglobin with oxygen (SPO2) signal data is synchronized with respiration signal data. One or more waveform parameters may be generated based on the synchronized SPO2 signal data and the respiration signal data. One or more respiration-SPO2 parameters may then be determined based on the one or more waveform parameters and used to characterize the biological tissue function.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
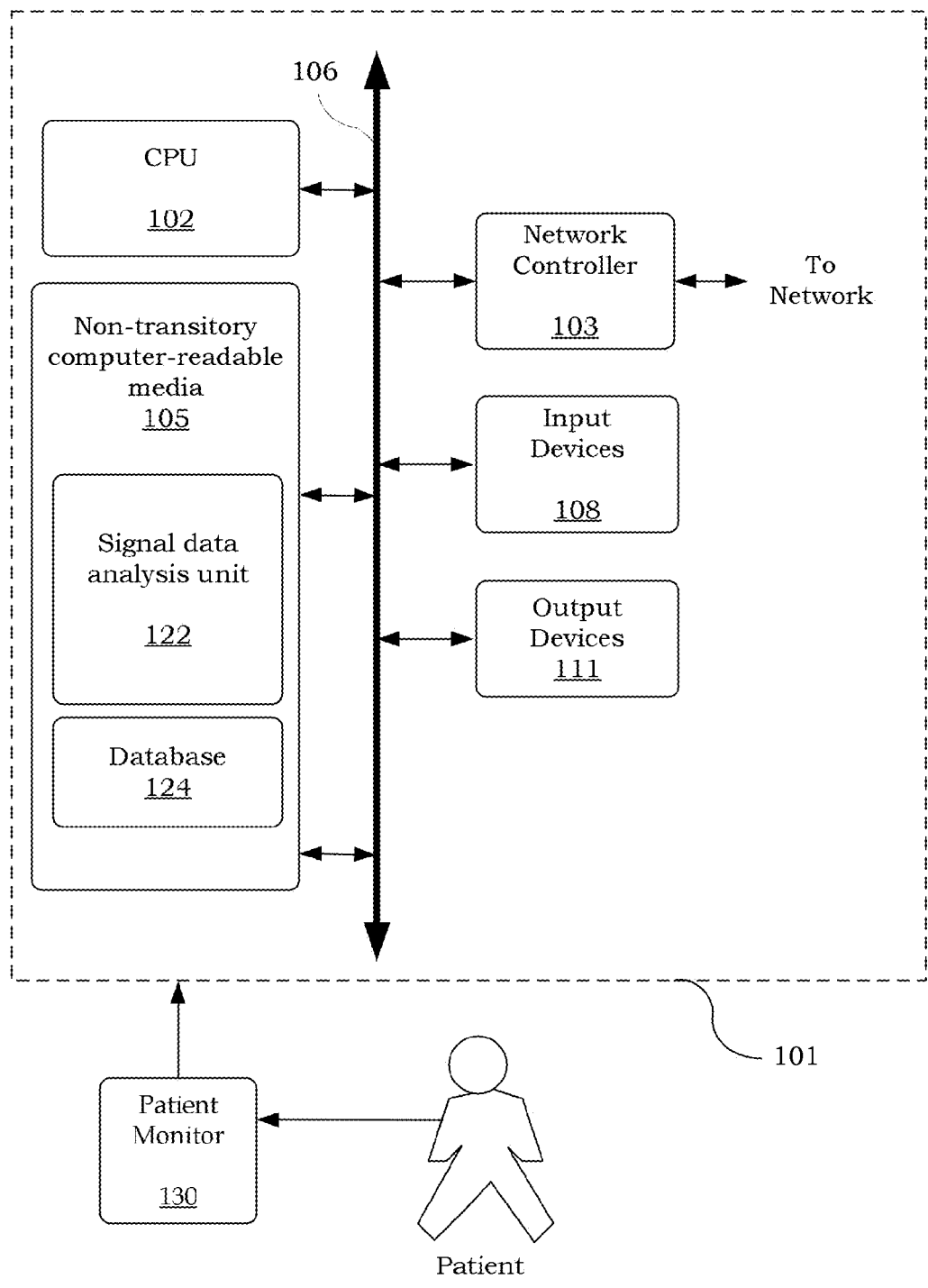
FIG. 1 shows an exemplary computer system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present framework advantageously provides a non-invasive approach for early detection, diagnosis, characterization and/or analysis of disorders, pathologies or abnormalities (e.g., arrhythmia, myocardial ischemia events, etc.). One aspect of the present framework analyzes signal data indicative of blood oxygen content in a patient's blood vessel. Such data may include SPO2 data indicative of saturation of hemoglobin with oxygen as measured by pulse oximetry. SPO2 signal data is one of the key measurements for vital signs commonly used to monitor and diagnose a patient's medical health status. The SPO2 signal may be synchronized with a respiration signal to diagnose and characterize hemodynamic signals and data variation in a patient. Known methods generally do not link SPO2 oximetric signal changes in small blood vessels (e.g., capillaries) with cardiac hemodynamic signals, contraction and activities during heart blood pumping and blood flow. Various implementations of the present framework analyze the SPO2 signal morphology fluctuating and changing rate to provide a new approach for quantitative and qualitative detection and characterization of cardiac arrhythmia.

In accordance with some implementations, SPO2 and respiration signals are synchronized and integrated to provide a set of parameters that may be used to detect, quantify and evaluate cardiac arrhythmia and/or hemodynamic function information (e.g., type, severity, trend, location, etc.) by calculating and characterizing oxygen transition mode and patterns in the patient circulation system (e.g., timing, speed, volume from lung to heart to capillary arteries, etc.). Various implementations of the framework may be used to facilitate identification of cardiac disorders, differentiation of cardiac arrhythmias, characterization of pathological severities, prediction of life-threatening events, and even evaluation of drug delivery and effects. The SPO2-respiration signal based cardiac arrhythmia detection and characterization described herein provides a methodology to much earlier and more efficiently detect and diagnose patient arrhythmias and pathology than traditional clinical methods (e.g., ECG signal waveform, blood pressure signal analysis, etc.). These and other features and advantages will be described in more detail herein.

For purposes of illustration, the present framework is described herein in the context of cardiac tissue functions and abnormalities. However, it should be appreciated that the present framework is also useful for analyzing other kinds of biological tissue functions, including detecting, characterizing and predicting any abnormalities and associated suitable treatments, such as respiration system pathology, brain injury due to cardiac abnormality, secondary injury, etc.

FIG. 1 shows an exemplary system 100 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), P2P, a global computer network (e.g., Internet), a wireless communications network, or any combination thereof. Given the teachings of the present invention provided herein, one of ordinary skill in the related art will be able to contemplate these and similar implementations or configurations of the present invention.

As shown in FIG. 1, the system 100 includes a computer system 101 and a patient monitor 130. The computer system 101 may include, inter alia, a central processing unit (CPU) 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The present techniques may be implemented by a signal data analysis unit 122 that is stored in computer-readable media 105. As such, the computer system 101 is a general-purpose computer system that becomes a specific purpose computer system when executing the computer-readable program code.

The same or different computer-readable media 105 may be used for storing a database 124. Database 124 may include a repository of determined parameters and ratios, selectable predetermined functions, SPO2 signal data, respiration signal data, electrophysiological signal data (e.g., ECG, ICEG, etc.), patient data (e.g., demographic data, pathology history, etc.), other input data and/or other derived output parameters. SPO2 signal data, respiration signal data and other electrophysiological signal data may be provided by a patient monitor 130 that is communicatively coupled to the computer system 101.

As shown in FIG. 1, system 100 may include a patient monitor 130 for monitoring various types of patient biometric or physiological signal information. For example, the monitored information can include, but is not limited to, SPO2 signal data, respiration signal data, heart rate (e.g., ECG, ICEG, etc.), blood pressure, temperature and other patient biometric, physiological or medical parameter information. The patient monitor 130 may include appropriate biometric sensors for sensing the desired patient information.

In some implementations, patient monitor 130 includes non-invasive oximeter (e.g., pulse oximeter). The oximeter may include non-invasive infrared light sensor system that acquires and outputs a continuous stream of oximetric data (SPO2) with sample rate of 20-100 Hz. Exemplary oximetric systems include, but are not limited to, the Massimo, Nellcor or Nonin oximeters. SPO2 oximetric signals are typically used to monitor oxygen content in the blood for diagnosis and characterization of the patient health status (e.g., detecting asthma). However, they can also be used to reflect the cardiac blood pumping and contraction activities of ventricles, especially the left ventricular functions. The digitized SPO2 signal data may be used to calculate and estimate SPO2 waveform characteristics and parameters for detecting cardiac abnormalities (e.g., ventricular arrhythmia) as well as any other types of abnormality.

The patient monitor 130 may further include a respiratory monitor for monitoring respiration signal waveforms associated with the patient. For example, patient monitor 130 may include a capnograph (e.g., Microcap commercially available from Oridion Ltd.) for measuring the carbon dioxide content in inspired and expired air from the patient. Respiration signal waveforms may be derived from such respiration measurements. Alternatively, such respiration signal waveforms may also be extracted from electrocardiography (ECG) lead impedance changing signal waveforms during respiration. Such respiration signal waveforms may be derived in real time and used to calculate and synchronize the non-invasive SPO2 signal cycles (e.g., timing and latency ratios). The synchronization of timing and latency between SPO2 signal waveforms and respiration signal waveforms may be used to track and capture the changes and distortion of oxygen usage and transmission in the blood flow.

Figure 2:
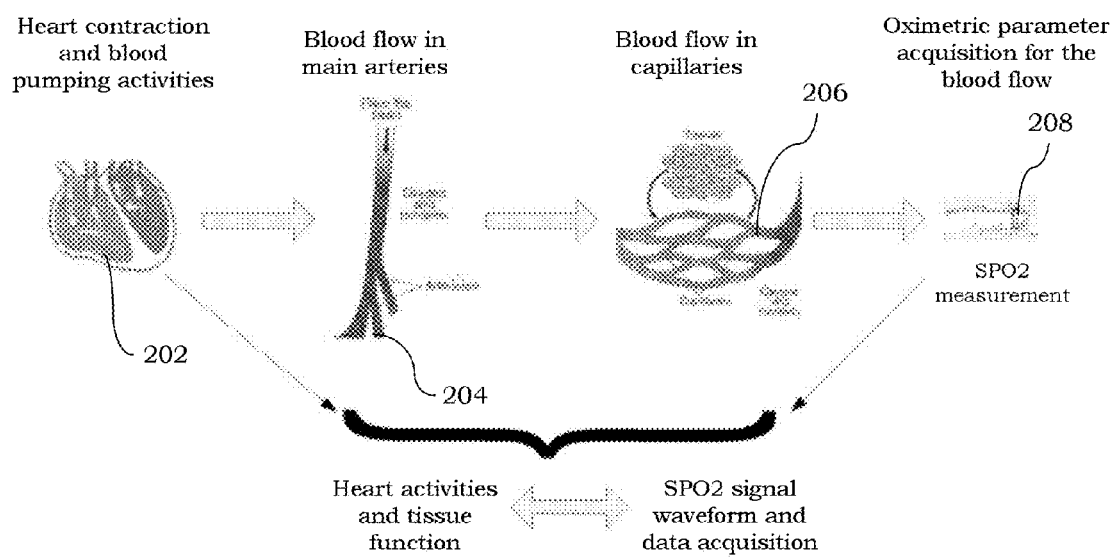
FIG. 2 is a schematic diagram of blood flow mapping.

FIG. 2 is a schematic diagram of blood flow mapping. More particularly, blood flow in a patient's body may be mapped from cardiac chambers in the heart 202 to main arteries 204 to body capillaries 206, such as those located at a fingertip 208 where a physician can measure SPO2 signals, waveform and parameters via, for example, an infrared light sensor placed on or near the capillaries 206. Typically, there are 4-10 heart beats in one respiration cycle and the oxygen level in blood usually indicates a fluctuating continuous curve in oxygen content, particularly in fingertip capillaries. Blood with oxygen flows to the left ventricle of the heart 202, and is pumped out by the heart's ventricular chambers to the main arteries 204, which transport the oxygenated blood to every other part of the body, including organs, big vessels, small vessels, and finally to capillaries 206. Therefore, SPO2 blood flow oximetric signal data measured at the capillaries 206 can reflect the cardiac functions and activities of the heart 202, such as myocardial contracting strength, energy, duration, etc.

In accordance with the present framework, cardiac functional characteristics may be non-invasively monitored, diagnosed and characterized by using SPO2-respiration signal-based waveform morphologies and related parameters. The present approach differs from traditional clinical applications and approaches, which focus only on the oxygen relative saturation rate information provided by SPO2 signal data and do not provide efficient methods and calculations for SPO2 morphology and shape diagnosis, or combine SPO2 signal data with real-time continuous respiration signals. In some implementations of the present framework, SPO2 signal morphology fluctuations and changing rate are used for quantitative and qualitative detection and characterization of cardiac arrhythmia properties, such as severity, type, location, trend, etc.

Figure 3:
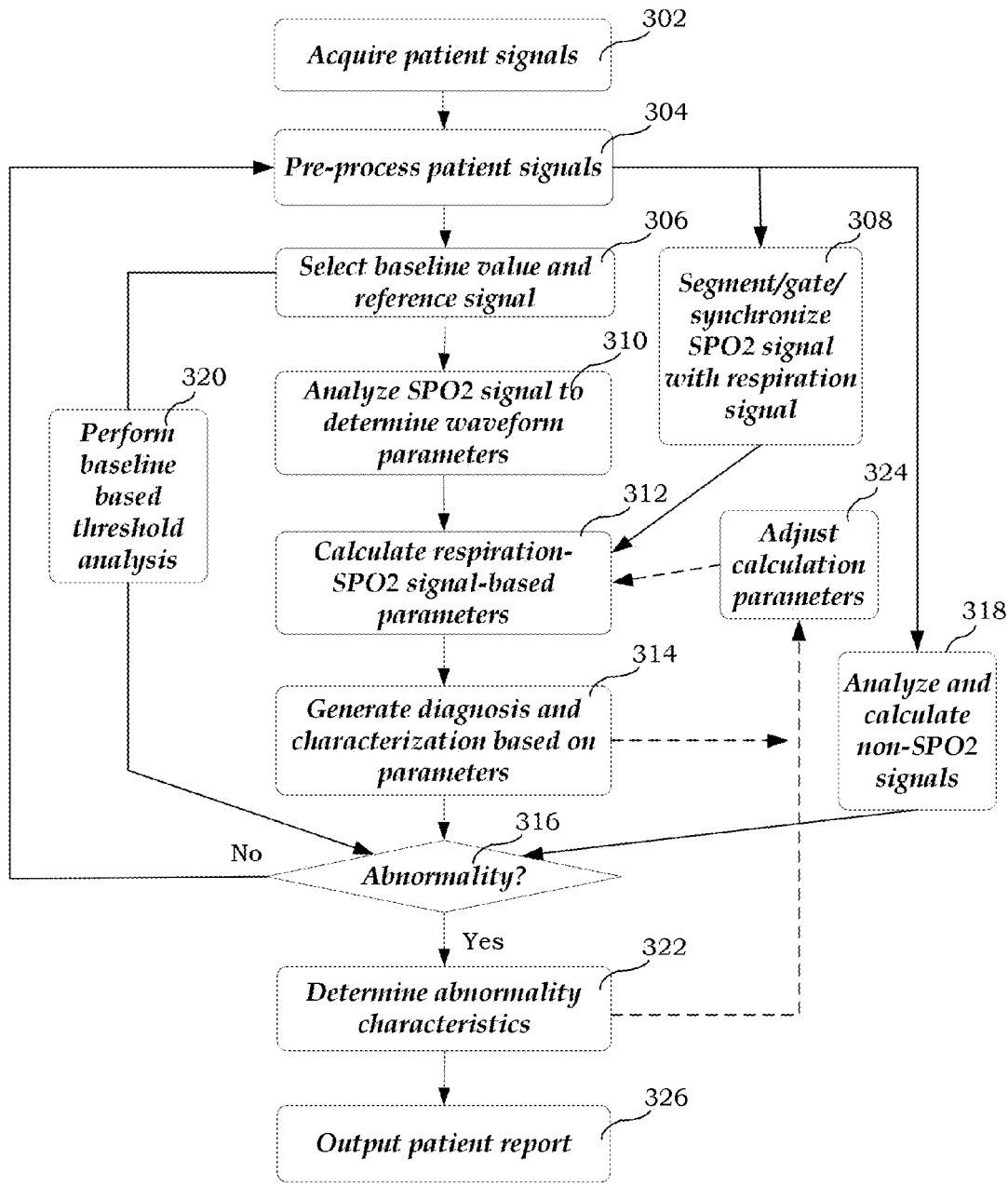
FIG. 3 shows an exemplary method of analyzing biological tissue functions.

FIG. 3 shows an exemplary method 300 of analyzing biological tissue functions, such as characterizing and detecting cardiac abnormalities. The steps of the method 300 may be performed in the order shown or a different order. Additional, different, or fewer steps may be provided. Further, the method 300 may be implemented with the system 100 of FIG. 1, a different system, or a combination thereof.

At 302, patient monitor 130 acquires patient signals associated with a current patient. Such patient signals may include, for example, oximetric (or SPO2), respiration (or capnographic), electrophysiological signals (e.g., ECG, ICEG), and so forth. Other types of patient signals, such as other vital sign signals (e.g., temperature), other measurable patient biometric, physiological or medical signals, patient information, such as demographic data, clinical application and patient status, including, but not limited to, weight, height, gender, age, allergies, medications, etc., may also be acquired.

At 304, patient monitor 130 pre-processes the patient signals. Patient monitor 130 may pre-process the patient signals by filtering, amplification, digitization and/or buffering. For example, the patient signals may be filtered and amplified for display on, for instance, patient monitor 130. The patient signals may be filtered to remove patient movement and respiratory artifacts, as well as power line noise. In some implementations, patient monitor 130 amplifies, buffers, filters and/or digitizes the patient signals to produce a continuous stream of digitized samples. The digitized patient signal samples or data are provided to signal data analysis unit 122 for processing.

At 306, signal data analysis unit 122 determines the baseline value and a reference signal of the SPO2 signal from the digitized patient signals. The baseline value (or level) generally refers to a known threshold value with which an unknown is compared when measured or assessed, while the reference signal is the signal received from a healthy patient. The baseline value may comprise a zero voltage line if a static (DC) voltage signal component is filtered out from the signal. The baseline value may be automatically, semi-automatically or manually selected by the user. It may be selected and adaptively adjusted according to the current application and clinical requirements.

At 308, signal data analysis unit 122 synchronizes (e.g., segments, gates, etc.) the SPO2 signal with the respiration signal from the digitized patient signals. In some implementations, this step 308 is performed substantially concurrently with step 310 to continuously process incoming patient signals. The respiration signal may be derived in real-time from the capnograph signal or other patient signals (e.g., chest impedance signal). The respiration signal is used to synchronize the SPO2 signal cycles and to calculate associated parameters (e.g., timing and latency ratios).

Figure 4:
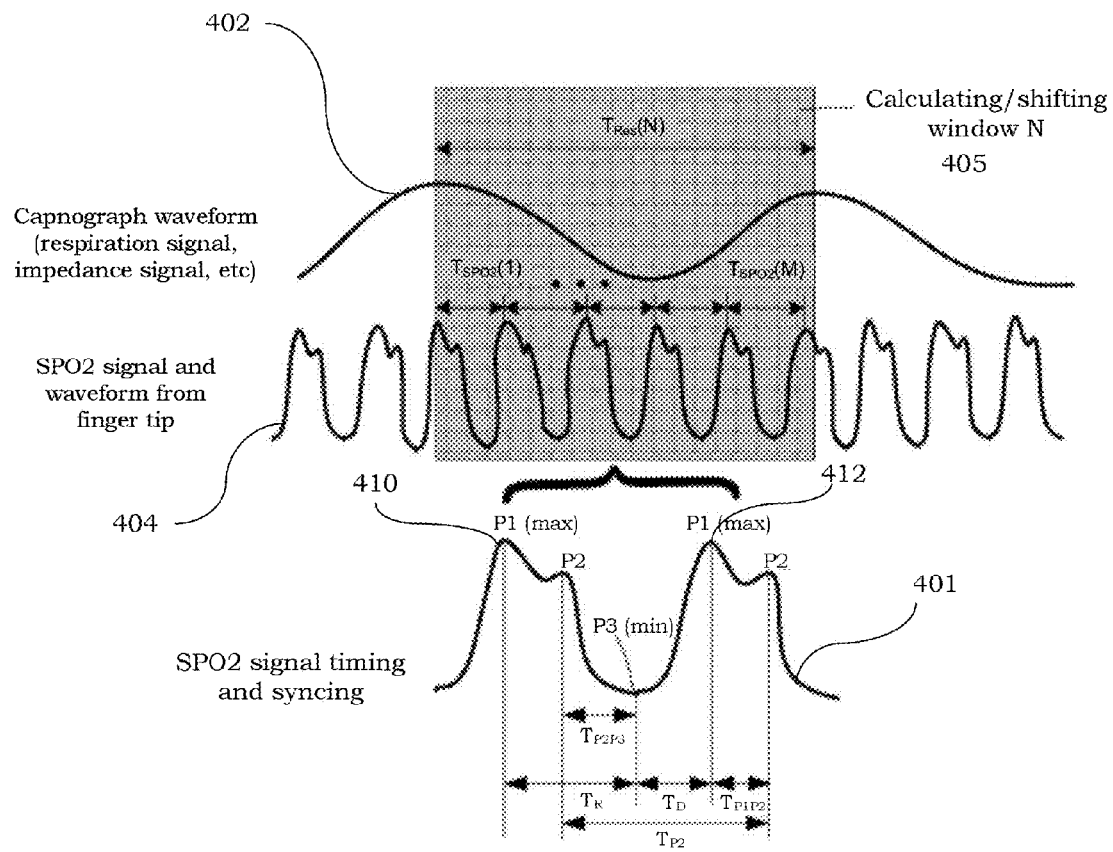
FIG. 4 illustrates an example of synchronization of SPO2 oximetric signal waveform with respiration signal waveform.

FIG. 4 illustrates an exemplary synchronization of SPO2 oximetric signal 404 with respiration signal 402. The respiration signal waveform 402 may be derived from, for example, a real-time chest impedance signal or capnographic signal. In a clinical application, SPO2 and respiration signal data may be acquired at the same time as synchronized signals. A calculation or shifting window N (405) may be synchronized with respect to a detected respiration cycle. Typically, within one respiration cycle, there may be 3-10 heart cycles corresponding to 3-10 SPO2 signal cycles. Due to cardiac arrhythmia or other heart malfunctions, the SPO2 timing and latency may be modified by cardiac blood contraction and reperfusion cycle variation. Therefore, the ratio of the timing intervals and latencies between respiration and SPO2 blood oximetric signals within the calculating window 405 may be determined and used to characterize cardiac pathologies, as will be described with reference to steps 312 and 314.

Alternatively, or additionally, the SPO2 signal itself may be segmented using respiration signal gating. For example, inspiration (or inhalation) and expiration (or exhalation) portions of the respiration signal may be used to select corresponding first and second SPO2 signal cycles. The first and second SPO2 cycles may be selected to capture, for instance, cardiac electrophysiological-hemodynamic characteristics, heart contraction-reperfusion tissue malfunction and an associated time stamp. If a heart and chamber blood flow circulation system of the patient has a malfunction or arrhythmia, the non-invasive SPO2 signal at the two different timing intervals (inspiration and expiration) of the respiration signal may show a difference in the SPO2 signal itself. Such difference may be utilized as a signature for cardiac function monitoring and analysis.

Figure 5:
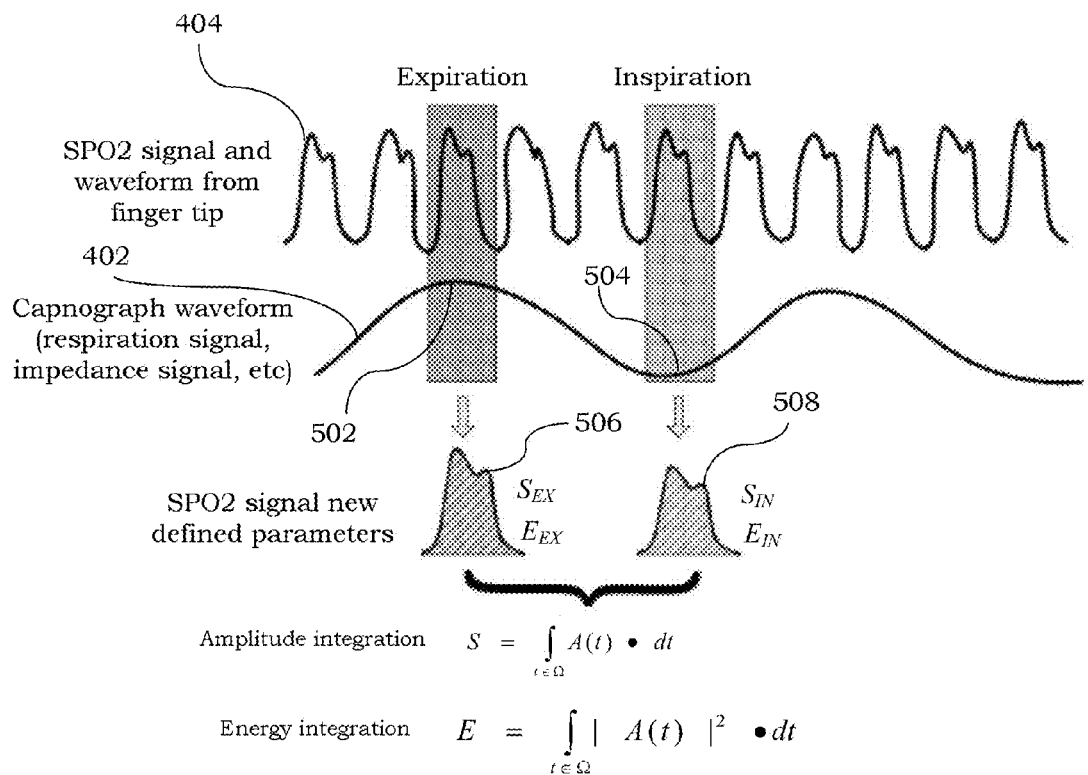
FIG. 5 shows an example of SPO2 signal cycle selection and characterization.

FIG. 5 shows an exemplary SPO2 signal 404 cycle selection and characterization by gating and synchronizing with expiration and inspiration portions (502 and 504) of the respiration signal 402. By gating and segmenting the SPO2 signal 404 using the respiration signal 402, optimum heart cycle SPO2 signals (506 and 508) may be determined and used for calculating parameters, such as a continuous amplitude and/or energy integration indices, as will be described with reference to step 312. Such inspiration and expiration timing-based respiration-SPO2 signal parameters may be utilized to detect, for example, ventricular myocardial ischemia-infarction and atrial fibrillation.

In FIG. 5, inspiration and expiration timings are determined using a capnograph signal 402 and waveform peak or valley detection. The capnograph signal (or equivalent) waveform 402 may be extracted from different sources, such as respiration monitoring devices, ECG or intra-cardiac lead impedance monitoring device, and/or from continuous patient signals, such as invasive and non-invasive blood pressure signals. Using peak and valley timing detection, corresponding SPO2 heart blood flow cycles (506 and 508) are captured.

Returning back to FIG. 3, at 310, signal data analysis unit 122 analyzes the SPO2 signal waveform to determine waveform parameters. Such analysis may be performed substantially continuously and in real-time. In addition, it should be appreciated that in some implementations, this step 310 is performed substantially concurrently with step 308 to continuously process incoming patient signals. Analyzing the SPO2 signal waveform may include detecting successive oximetric cycles, detecting different predetermined segments (or sections) within a heart (or heartbeat) cycle of a repetitive waveform, extracting morphology information, calculating amplitude and/or energy integration parameters, and/or other waveform parameters. Morphology information may include amplitude and timing information of consecutive peaks and valleys within a predefined SPO2 wave or cycle (e.g., from one maximum peak to the next maximum peak).

FIG. 4 illustrates an exemplary synchronized SPO2 signal waveform 401 from which the waveform parameters may be derived. The synchronized SPO2 signal waveform 401 may be obtained by synchronizing the SPO2 signal 404 acquired from the finger tip of the patient with the respiration signal 402 acquired from the same patient, as previously described with respect to step 308.

The acquired SPO2 signal 404 may be segmented into detection windows where waves are expected and peaks and/or valleys within the windows may be identified. The segmentation may be performed by synchronizing a detection window with respect to detected cycle start or end points. Referring to FIG. 4, for instance, a cycle start point 410 may be defined by a maximum peak of the signal and the cycle end point 412 may be defined by the next consecutive maximum peak of the signal. Alternatively, the cycle start and end points may be the minimum valleys of the signal, the points where the signal crosses the baseline value (in a predetermined wave window, for example) or any other pre-defined points. The start and/or end points of the cycle may be identified by a variety of known different methods.

A peak and/or valley detector may be provided in the signal data analysis unit 122 for detecting P1 (maximum peak value), P2 (second consecutive peak value) and P3 (minimum value) in the waveform within the synchronized SPO2 signal 401. A timing detector may further be provided in the signal data analysis unit 122 for determining time durations (e.g., $T_R$, $T_D$, $T_{P1P2}$, $T_{P2P3}$, $T_{P2}$, $T_{SPO2}(1)$ ... $T_{SPO2}(M)$, etc.) between the signal peaks (e.g., P1, P2, etc.) and valleys (e.g., P3, etc.). The timing detector may use a clock counter for counting a clock between the peak and valley points, and the counting may be initiated and terminated in response to the detected peak and valley characteristics.

In some implementations, amplitude and/or energy integration parameters may be extracted from the selected first and second cycles (506 and 508) of the synchronized and gated SPO2 signal, as shown in FIG. 5. Such SPO2 parameters may be computed as follows:

$$\text{Amplitude integration } S = \int_{t \in \Omega} A(t) \cdot dt \quad (1)$$

$$\text{Energy integration } E = \int_{t \in \Omega} |A(t)|^2 \cdot dt \quad (2)$$

where Ω is the selected SPO2 heart cycle (506 or 508) which is gated by the inspiration or expiration portion of the respiration signal 402; and A(t) are the continuously recorded SPO2 amplitude values in cycle Ω. Cardiac arrhythmias and malfunctions may advantageously be detected by comparing these SPO2 parameters between the two specific cycles to advantageously improve patient safety and reduce treatment delay.

Turning back to FIG. 3, at 312, signal data analysis unit 122 calculates respiration-SPO2 signal-based ratios, indices and other parameters based at least in part on the waveform parameters. Respiration-SPO2 signal-based ratios may include, for example, respiration-SPO2 signal cycle and timing ratios, inhalation (or inspiration) and exhalation (or expiration) SPO2 amplitude and energy indices, and so forth. Other parameters, such as statistical parameters (e.g., mean, standard deviation, SPO2 signal ratio variation, SPO2 signal ratio variability, etc.) may further be derived.

In some implementations, a respiration-SPO2 signal cycle ratio may be calculated as follows:

$$\text{Respiration-}SPO2\_\text{cycle\_ratio}(N) = \frac{T_{Res}(N)}{E(T_{SPO2})} = \frac{T_{Res}(N)}{\frac{1}{M}\sum_{i \in M} T_{SPO2}(i)} \quad (3)$$

where N denotes a number in a sequential series; $T_{Res}(N)$ is the number N cycle time duration of the respiration signal waveform 402 (e.g., measured from peak to peak as shown in FIG. 4, but it can be valley to valley in the signal waveform 402); $T_{SPO2}$ is the SPO2 signal cycle time duration (e.g., measured from peak to peak); and $E(T_{SPO2})$ is the mean time duration of SPO2 signal cycles (average or expectation within the shifting window N) that correspond to the number N respiration cycle in the shifting window 405. In the example shown in FIG. 4, there are M SPO2 signal cycles occurring with the Nth respiration signal cycle within the shifting window 405.

In some implementations, a respiration-SPO2 signal timing ratio may be calculated as follows:

$$\text{Respiration-}SPO2\_\text{timing\_ratio}(N) = \frac{T_{Res}(N)}{E(X_{SPO2})} = \frac{T_{Res}(N)}{\frac{1}{M}\sum_{i \in M} X_{SPO2}(i)} \quad (4)$$

where $X_{SPO2}$ is one of the timing intervals or latencies from an SPO2 signal waveform segment, such as $T_R$, $T_{P2P3}$, $T_D$, etc. By analyzing the respiration-SPO2-timing-ratio, timing and latency changes in an SPO2 waveform portion due to cardiac function (not respiration) are accurately quantified and characterized.

In some implementations, a continuous amplitude integration index is calculated as follows:

$$SPO2-\text{Amplitude\_integration\_index}(N) = \frac{S_{Expiration\text{-}SPO2}}{S_{Inspiration\text{-}SPO2}} \quad (5)$$

wherein $S_{Expiration\text{-}SPO2}$ and $S_{Inspiration\text{-}SPO2}$ are amplitude integration parameters of selected SPO2 expiration and inspiration cycles (506 and 508) respectively, gated by the respiration signal 402, as illustrated by FIG. 5.

Similarly, a continuous energy integration index may be calculated as follows:

$$SPO2-\text{Energy\_integration\_index}(N) = \frac{E_{Expiration\text{-}SPO2}}{E_{Inspiration\text{-}SPO2}} \quad (6)$$

wherein $E_{Expiration\text{-}SPO2}$ and $E_{Inspiration\text{-}SPO2}$ are energy integration parameters of selected SPO2 expiration and inspiration cycles (506 and 508) respectively, gated by the respiration signal 402, as illustrated by FIG. 5.

Compared to conventional SPO2 waveform calculation and diagnosis that mostly focus on oxygen saturation analysis, there are at least two exceptional advantages of these respiration-SPO2 signal-based parameters over traditional parameters: sensitivity and stability in calculation, particularly in noisy environment and low perfusion blood flow cases (e.g., neonatal patients).

Figure 6:
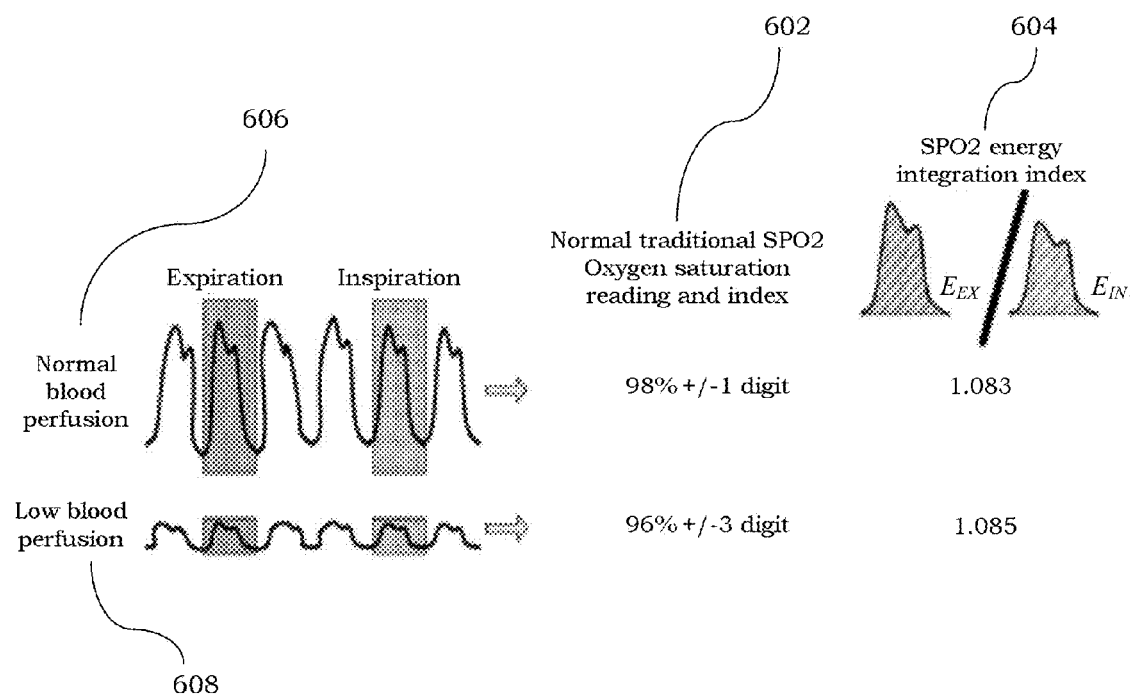
FIG. 6 illustrates an exemplary comparison between traditional SPO2 signal oxygen saturation-based index and the present SPO2 energy integration index.

FIG. 6 illustrates an exemplary comparison between traditional SPO2 signal oxygen saturation-based index 602 and the present SPO2 energy integration index 604 in two episodes with normal (100%) blood perfusion 606 and low (2%) blood perfusion 608. It was found that traditional methods using oxygen saturation index 602 could not detect any early information of the arrhythmia, while the present SPO2 energy integration index 604 detected early abnormalities of cardiac malfunction.

In this example, an SPO2 simulator was used for controlling the blood flow perfusion status: 100% vs. 2%. It was found that traditional SPO2 waveform oxygen saturation index 602 has a value of 98%+/−1 digit at normal blood perfusion and a value of 96%+/−3 digits at low blood perfusion. This may indicate that oxygen saturation shows more variation in low blood flow episodes, and may not be stable for use in diagnosis. In contrast, by using the present SPO2 energy integration index 604 based on selected expiration and inspiration heart cycles, good stability and sensitivity is provided, with less than 1% variation at both normal and low blood flow episodes. In other words, the present SPO2 parameter calculation 604 provides better stability in cardiac function analysis than the SPO2 oxygen index 602 which cannot characterize cardiac functions with high noise sensitivity and stability.

In accordance with some implementations, statistical parameters may be derived based on the respiration-SPO2 signal-based parameters over a plurality of heart cycles. For example, the following statistical parameters may be derived:

$$\text{Mean or average value(expectation): } \text{mean}(X) = \frac{1}{W}\sum_{i \in W} X(i) \quad (7)$$

$$\text{Standard deviation: } STD(X) = \frac{1}{W-1}\sum_{i \in W-1}(X(i) - \text{mean}(X)) \quad (8)$$

$$SPO2 \text{ signal ratio variation: } Var(X) = \frac{\text{mean}(X)}{STD(X)} \quad (9)$$

$$SPO2 \text{ signal ratio variability: } Var\_b = \frac{\max(X - \text{mean}(X))}{\text{mean}(X)} \quad (10)$$

wherein X is a respiration-SPO2 parameter (e.g., respiration-SPO2 signal cycle or timing ratio, inspiration or expiration SPO2 amplitude or energy integration index, etc.) as previously described; and W is the calculation window size. There may be W heart cycles in the shifting calculation window N. The heart cycles may also be derived directly from the SPO2 signal. In accordance with some implementations, the statistical calculation and evaluation of the patient SPO2 signal may further include high order statistical calculation (HOS), tests methods (such as t-test) and hypothesis evaluations of the signals/data distributions.

Returning back to FIG. 3, at 314, signal data analysis unit 122 generates a diagnosis and/or characterization based on the determined respiration-SPO2 signal-based parameters. Mapping information may be employed to associate determined parameters with characteristics of medical conditions.

At 318, non-SPO2 signals (e.g. ECG, ICEG, blood pressure, temperature, etc.) are analyzed by performing signal segmentation into predetermined sections (such as Q, R, S, T, U wave segments) within a heart cycle and performing morphology analysis to identify maximum and minimum values. Signal data analysis unit 122 may segment, analyze and use ECG and blood pressure signals in determining synchronized signal time durations and using the ECG and blood pressure signal parameters in combination with the SPO2 data in evaluating patient health status. The received ECG and blood pressure signals may also be analyzed to determine variations in signal parameters indicative of substantial change.

At 320, baseline-based threshold analysis is performed to determine threshold values for comparison. The analysis may be performed automatically and adaptively by signal data analysis unit 122. Alternatively, the user may manually perform the analysis.

At 316, signal data analysis unit 122 determines whether there is an abnormality. The abnormality may be, for example, a cardiac medical condition such as cardiac arrhythmia, cardiac tissue and electrophysiological-hemodynamic malfunctions, etc. In some implementations, the abnormality is identified based on baseline values and threshold values provided in step 320. For example, determined respiration-SPO2 signal-based parameters may be compared with the baseline and/or threshold values to determine if an abnormality exists.

Additionally, or alternatively, non-SPO2 signal data provided by step 318 may also be used to determine the presence of an abnormality. Although, in most cases, one or more respiration-SPO2 signal-based parameters provided by step 312 can provide good sensitivity and stability for detecting and diagnosing abnormalities, the accuracy and reliability of the diagnosis may be improved by combining these parameters with other types of patient data, such as ECG signal analysis, non-invasive blood pressure (NIBP) or invasive blood pressure (IBP) signal analysis, different lead ECG signals, different lead ICEG signals, and so forth.

At 322, signal data analysis unit 122 uses mapping information to determine the severity, type and/or location of the abnormality. Further health status evaluation and characterization, such as effects of drug delivery, treatment, etc., may be performed. At 326, a patient report or message may be generated to indicate the abnormality and associated characteristics. The patient report may be in the form of, for example, alert message presented at patient monitor 130. The patient report may be stored in database 124 for future retrieval.

In some implementations, signal data analysis unit 122 optionally adaptively adjusts calculation parameters at step 324 used for calculating the aforementioned parameters. The adaptive adjustment may be performed automatically, semi-automatically or manually by the clinical user. Such calculation parameters include, but are not limited to, time window, window shift step, number of samples in a calculation window, selected portions and region of interest (ROI) of a filtered signal, threshold employed to improve medical condition detection, and so forth. In the case of ventricular arrhythmia analysis, for example, a severity threshold, calculation time step and monitored tissue location may be selected in response to user command or automatic system adaptive adjustment. If an abnormality is not identified at step 316, the process 300 repeats from step 304.

In accordance with some implementations, an artificial neural network (ANN) is used for nonlinear data fusion and combination of different types of patient data, including the parameters, ratios and indices, as aforementioned. By using multiple-channels and/or multiple-kinds of patient data, cardiac arrhythmia can be more efficiently detected and characterized. For instance, cardiac pathology position may be identified, cardiac arrhythmia types may be differentiated, pathological severities may be characterized, life-threatening events may be predicted, drug delivery and effects may be evaluated, and so forth.

Figure 7:
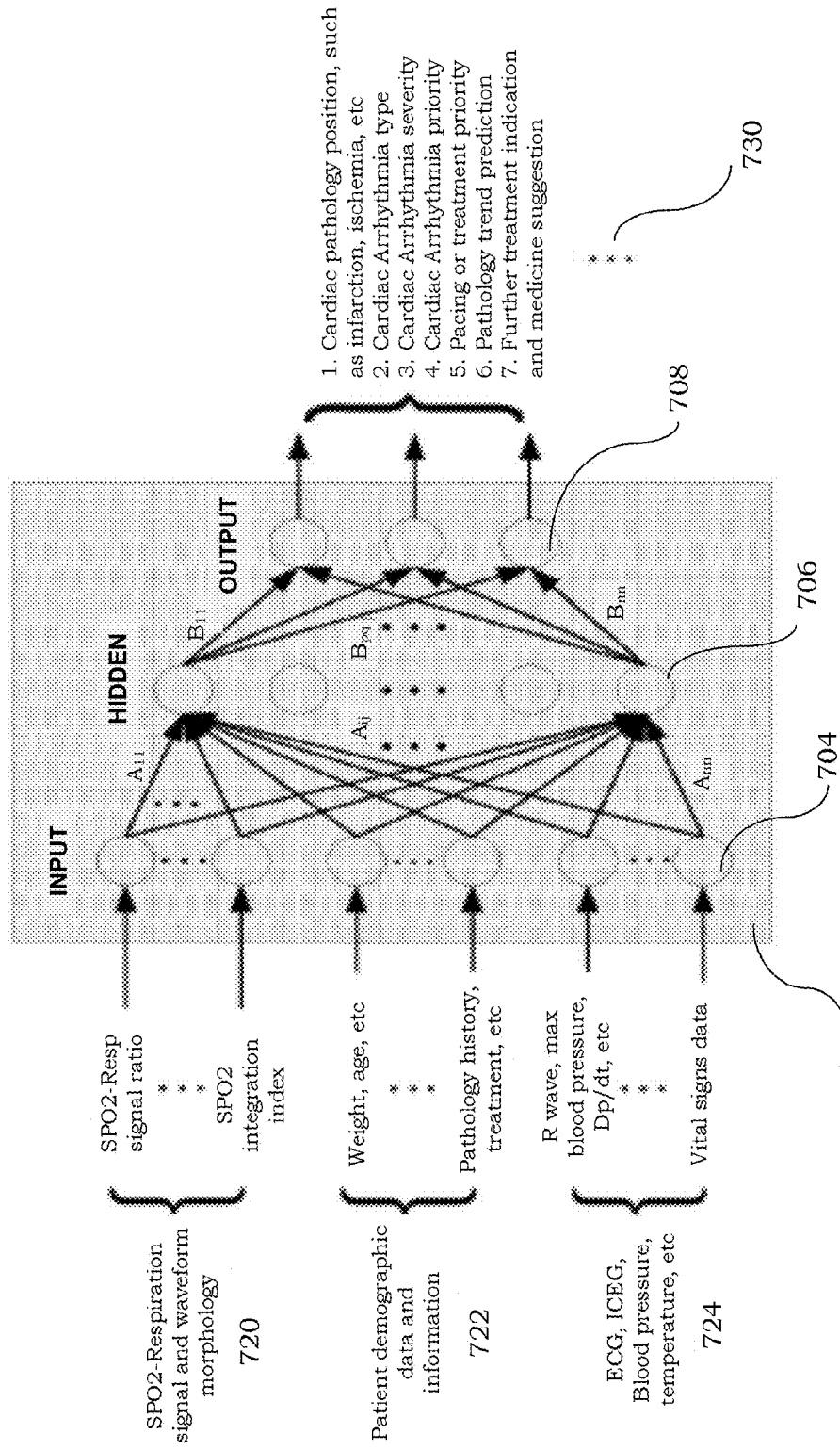
FIG. 7 shows an exemplary artificial neural network (ANN) structure for integrating multiple types of patient data.

FIG. 7 shows an exemplary ANN structure 702 for integrating multiple types of patient data for providing decision support in diagnosis and treatment of cardiac pathologies and arrhythmia and analysis of tissue function. Exemplary ANN structure 702 includes three layers—input layer 704, hidden layer 706 and output layer 708—for combining and integrating different kinds of SPO2-respiration signal amplitude, waveform parameters and associated ratios, indices and parameters 720, patient demographic data and other information 722 and other patient signal information (e.g., ECG, ICEG, blood pressure and other vital sign parameters) 724. ANN structure 702 combines and maps patient information 720, 722 and 724 to output parameters 730. Output parameters 730 may indicate, for example, cardiac pathology position (e.g., infarction, ischemia, etc.), cardiac arrhythmia type, severity and/or priority, pacing or treatment priority, pathology trend prediction, further treatment or medicine suggestion, and so forth. Such output parameters 730 may be used for the detection, diagnosis, warning and/or treatment of cardiac abnormalities. They may be used in different clinical applications, such as in operating room (OR) monitoring, ICU/CCU critical monitoring and emergency room (ER) patient status and health monitoring.

$A_{ij}$ are weights applied between the input layer 704 and the hidden layer 706, while $B_{pq}$ are weights applied between the hidden layer 706 and output layer 708 of the ANN computation. $A_{ij}$ weights and $B_{pq}$ weights are adaptively adjusted and tuned using a training data set. ANN unit 702 incorporates a self-learning function that processes new input data 720, 722 and 724 to increase the precision and accuracy of calculated results. The exemplary ANN-based analysis may combine SPO2-respiration signal analysis results with information derived from a medical professional's experience (input and suggested controlling mode) to greatly improve the sensitivity, specificity, stability and reliability of non-invasive methods.

Figure 8:
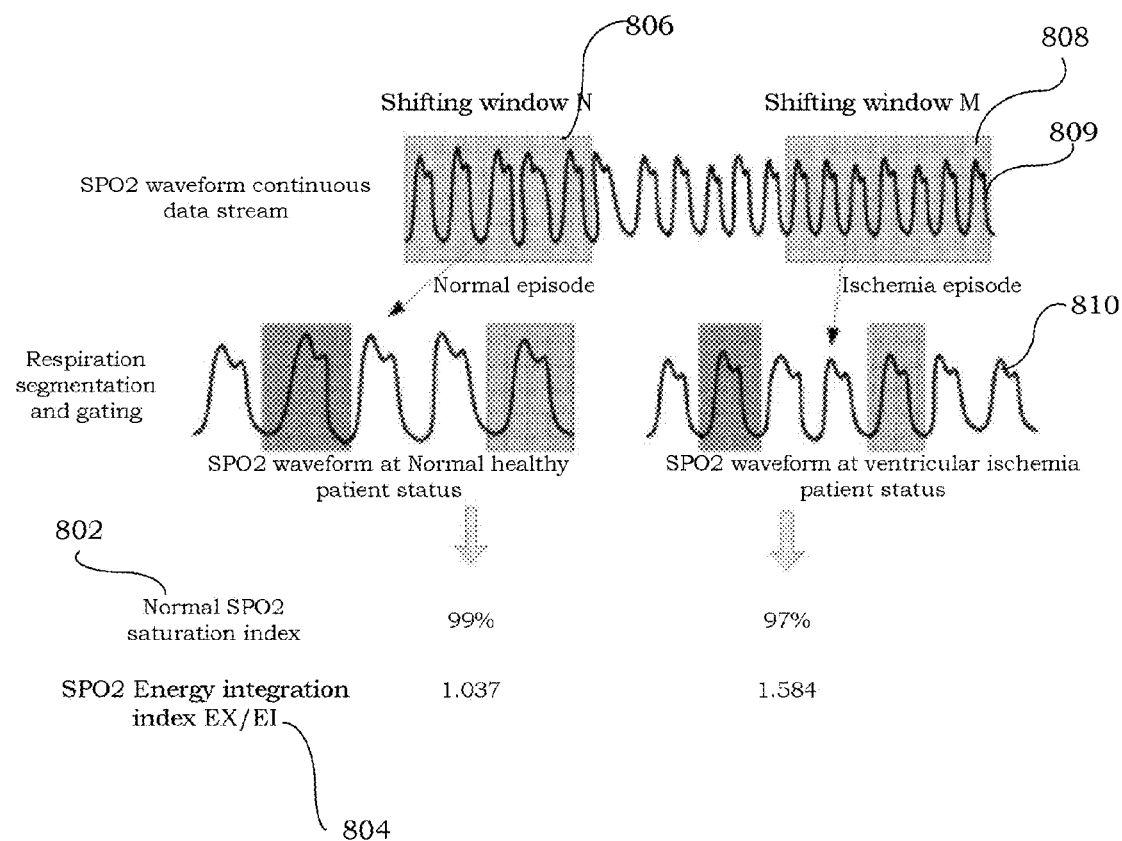
FIG. 8 illustrates exemplary SPO2 signal-based myocardial ischemia event calculations.

FIG. 8 illustrates exemplary SPO2-signal-based myocardial ischemia event calculations with computer simulated signals and data stream. In the example, ventricular arrhythmia was determined based on SPO2 signals associated with two different conditions: normal healthy status (or rest status) and ischemia status in left ventricle (or exercise status). The heart rate was 60 bpm in healthy status and 80 bmp during ischemia status.

Two sets of indices were calculated for each of these two conditions: traditional SPO2 saturation index 802 and SPO2 energy integration index (expiration/inspiration) 804 determined in accordance with the principles described herein. More particularly, the SPO2 energy integration index 804 was determined by gating and synchronizing the SPO2 signal 809 with the respiration signal 810. The calculating window size for rest status (window N) was set to 5, while the calculating window size for exercise status (window M) was set to 7 due to same time length for all the analysis. This window size change helped to eliminate the noise in the calculation caused by ischemia events, such as baseline changes.

It can be observed from the result that during the normal healthy status (window N) 806, the traditional SPO2 saturation index 802 was 99% while the SPO2 energy integration index 804 was 1.037. During the ischemia status (window M)

808, the traditional SPO2 saturation index 802 was 97% while the SPO2 energy integration index 804 was 1.584. Accordingly, the results indicate that the traditional SPO2 saturation index 802 may not be able to detect and characterize the ischemia status, especially in the early stage of myocardial ischemia. The SPO2 energy integration index 804, on the other hand, showed more than 50% difference in value between the two conditions, and is thus more efficient and reliable for ischemia detection. It should be appreciated that other SPO2-respiration-based parameters derived according to the principles of the present framework may also be used to efficiently and effectively detect ischemia or other abnormalities.

In this example, different kinds of SPO2 oximetric (from fingertip, forehead, internal heart, etc.) waveform analysis may help the medical practitioner to diagnose and estimate the ventricular pathologies and health status of the patient. Additionally, a threshold may be set and adjusted to track the cardiac function pathology by comparing to benign or pre-selected baseline signals (such as healthy status). For example, a 30% threshold may be set to detect an early infarction event and 10% threshold may be used to warn of ischemia events. By using different kinds of threshold, the SPO2-respiration signal calculation-based ventricular arrhythmia detection can be used to predict event occurrences and trends of cardiac rhythm, and even facilitate drug delivery and treatment.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A method for heart function analysis, comprising:
   receiving, by a processor, patient signal data from a patient, the patient signal data including SPO2 signal data received from an oximeter and indicative of saturation of hemoglobin with oxygen and respiration signal data received from a respiratory monitor;
   using a signal data analysis unit to synchronize the SPO2 signal data by gating the SPO2 signal using the respiration signal to select a first cycle of the SPO2 signal which corresponds to exhalation of the patient and a second cycle of the SPO2 signal which corresponds to inspiration of the patient;
   determining, by the processor, one or more waveform parameters based on the selected cycles of the synchronized SPO2 signal data;
   determining, by the processor, one or more respiration-SPO2 parameters based on the one or more waveform parameters;
   determining a heart function based on the one or more respiration-SPO2 parameters; and
   generating a patient report indicating the determined heart function.

2. The method of claim 1 wherein determining the one or more waveform parameters comprises extracting morphology information associated with the synchronized SPO2 signal.

3. The method of claim 2 wherein extracting the morphology information comprises detecting peaks or valleys of a waveform within the synchronized SPO2 signal and determining time durations between the peaks or valleys.

4. The method of claim 3 wherein determining the one or more respiration-SPO2 parameters comprises calculating a cycle ratio based on a respiration signal cycle time duration and a mean time duration of SPO2 signal cycles within the synchronized SPO2 signal.

5. The method of claim 3 wherein determining the one or more respiration-SPO2 parameters comprises calculating a timing ratio based on a respiration signal cycle time duration and a mean value of the determined time durations associated with the synchronized SPO2 signal.

6. The method of claim 1 wherein determining the one or more waveform parameters comprises determining an amplitude integration parameter associated with the selected first or second cycle.

7. The method of claim 6 wherein determining the one or more respiration-SPO2 parameters comprises calculating an amplitude integration index based on a first amplitude integration parameter associated with the selected first cycle and a second amplitude integration parameter associated with the selected second cycle.

8. The method of claim 1 wherein determining the one or more waveform parameters comprises determining an energy integration parameter associated with the selected first or second cycle.

9. The method of claim 8 wherein determining the one or more respiration-SPO2 parameters comprises calculating an energy integration index based on a first energy integration parameter associated with the selected first cycle and a second energy integration parameter associated with the selected second cycle.

10. The method of claim 1 wherein determining the heart function comprises characterizing cardiac arrhythmia.

11. The method of claim 10 wherein characterizing the cardiac arrhythmia comprises identifying a severity, type or location of the cardiac arrhythmia.

12. The method of claim 1 further comprising performing a statistical evaluation of the one or more respiration-SPO2 parameters over a plurality of heart cycles.

13. The method of claim 12 wherein performing the statistical evaluation comprises calculating a mean, standard deviation, variation or variability.

14. The method of claim 1 further comprising acquiring the SPO2 signal data by pulse oximetry.

15. The method of claim 1 further comprising acquiring the respiration signal data by using a capnograph.

16. The method of claim 1 further comprising extracting the respiration signal from electrocardiography signal waveforms during respiration.

17. The method of claim 1 further comprising using an artificial neural network to combine the respiration-SPO2 parameters with other types of patient data to generate output parameters that are used to characterize the biological tissue function.

18. A non-transitory computer readable medium embodying a program of instructions executable by machine to perform steps for heart function analysis, the steps comprising:
   receiving patient signal data from a patient, the patient signal data including SPO2 signal data received from an oximeter and indicative of saturation of hemoglobin with oxygen and respiration signal data received from a respiratory monitor;
   using a signal data analysis unit to synchronize the SPO2 signal data by gating the SPO2 signal using the respiration signal to select a first cycle of the SPO2 signal which corresponds to expiration of the patient and a second cycle of the SPO2 signal which corresponds to inspiration of the patient;

determining one or more waveform parameters based on the selected cycles of the synchronized SPO2 signal data;
determining one or more respiration-SPO2 parameters based on the one or more waveform parameters;
determining a cardiac arrhythmia classification based on the one or more respiration-SPO2 parameters; and
generating a patient report indicating the determined cardiac arrhythmia classification.

19. A system for heart function analysis, comprising:
a patient monitor comprising an oximeter and a respiratory monitor, the patient monitor for receiving patient signal data from a patient, the patient signal data including SPO2 signal data acquired by the oximeter and indicative of saturation of hemoglobin with oxygen and respiration signal data acquired by the respiratory monitor;
a signal data analysis unit for synchronizing the SPO2 signal data by:
  gating the SPO2 signal using the respiration signal to select a first cycle of the SPO2 signal which corresponds to expiration of the patient and a second cycle of the SPO2 signal which corresponds to inspiration of the patient;
  determining one or more waveform parameters based on the selected cycles of the synchronized SPO2 signal data;
  determining one or more respiration-SPO2 parameters based on the one or more waveform parameters;
  determining a heart function based on the one or more respiration-SPO2 parameters; and
an output device for presenting a patient report indicating the determined heart function.

* * * * *